(12) United States Patent
Duncan et al.

(10) Patent No.: US 7,894,069 B2
(45) Date of Patent: Feb. 22, 2011

(54) RESPIRATOR END-OF-SERVICE LIFE PROBE

(75) Inventors: E. J. Scott Duncan, Alberta (CA); David B. Pedersen, Alberta (CA)

(73) Assignee: Her Majesty the Queen in right of Canada, as represented by the Minister of National Defence of Her Majesty's Canadian Government, Ottawa, Ontario (CA)

( * ) Notice: Subject to any disclaimer, the term of this patent is extended or adjusted under 35 U.S.C. 154(b) by 519 days.

(21) Appl. No.: 12/078,976

(22) Filed: Apr. 9, 2008

(65) Prior Publication Data

US 2010/0284010 A1    Nov. 11, 2010

(51) Int. Cl.
*G01N 21/00* (2006.01)
(52) U.S. Cl. ...................................... 356/432; 356/437
(58) Field of Classification Search ......... 356/432–440, 356/442–443; 128/202.22; 73/23.2, 705; 55/DIG. 33–DIG. 35; 95/25, 268; 96/417–418, 96/FOR. 170; 385/12–13
See application file for complete search history.

(56) References Cited

U.S. PATENT DOCUMENTS 6,375,725 B1 *    4/2002    Bernard et al. ................ 96/417

* cited by examiner

*Primary Examiner*—Gregory J Toatley
*Assistant Examiner*—Tri T Ton
(74) *Attorney, Agent, or Firm*—George A. Seaby

(57) ABSTRACT

An end-of-service life indicator for a sorbent filter includes a tube containing a noble metal nanoparticle film on an optically transparent substrate, the substrate being perpendicular to the axis of the tube. An opening in the tube adjacent to the film allows chemical vapor to accumulate in the tube and be absorbed by the film. A light source located at one end of the tube and a light detector at the other end determines the amount of light absorbed by the nanoparticle film due to exposure to chemical vapor. A signal from the light detector is applied to an electronic processor that determines attenuation of light by the film, and the processor is connected to an indicator to provide an indication of the exposure of the film to the vapor.

14 Claims, 3 Drawing Sheets

US 7,894,069 B2

RESPIRATOR END-OF-SERVICE LIFE PROBE

FIELD OF THE INVENTION

This invention relates to an end-of-service life indicator for a filter containing a gas/vapor sorbent bed such as activated carbon.

The indicator of the present invention is used in a detector to detect saturation of a sorbent bed by chemical vapors to which the sorbent bed has been exposed. The indicator has an improved non-selective sensitivity to the vapors.

BACKGROUND OF THE INVENTION

Respirator canisters or cartridges are used to protect the health of military personnel, first responders and industrial workers from aerial chemical vapors. More than ten million respirator cartridges are being used each day in North America. It is desirable that a respirator canister includes an active indicator to indicate without ambiguity that the useful life of a canister has ended. However, currently commercially available canisters that protect against chemical vapors are not equipped with such an indicator. Without a device to monitor the sorption efficiency or protection provided by a canister to vapor penetration, a situation may arise where the sorption capacity of the canister is exceeded, rendering the canister ineffective and providing no protection without the user being aware that protection is no longer available.

Dye-based sensors to determine the remaining adsorption life of activated carbon in a canister exist, but these rely on a chemical reaction occurring with absorbed gases and are therefore limited to gases which undergo chemical reactions with the dyes.

The Eian U.S. Pat. No. 4,326,514 described a respirator canister or cartridge containing a gas/vapor sorbent bed with a colorimetric indicator strip positioned along a portion of an inner transparent sidewall of the cartridge. The colorimetric indicator is viewable through the transparent sidewall. The colorimetric indicator undergoes an irreversible change in color upon exposure to concentrations of select toxic vapors to which the sorbent bed is exposed. The indicator is effective at indicating the remaining capacity of the sorbent bed for toxic airborne material The indicator is, however, limited to toxic airborne material that undergoes a chemical reaction with the indicator strip.

The Bernard et al U.S. Pat. No. 6,375,725 described an end-of-service indicator for a respirator canister or cartridge having a gas/vapor sorbent bed (such a activated carbon) with an optical waveguide (optical fiber) located in the sorbent bed. One extremity of the waveguide is connected to a light source and the other to alight detector which measures the intensity of light transmitted by the waveguide. A portion of the outer layer of the waveguide is porous so that when the respirator cartridge is used in a toxic environment, the gas/vapor sorbent and the porous portion of the fiber gradually become saturated with absorbed gases. With absorption into the porous portion, the transmission of light through the fiber decreases. The detector senses the decrease in transmitted light and sends a signal to sound an alarm when the intensity of light measured by the detector is below a predetermined level. That alarm indicates that the sorbent is saturated and that the cartridge is at its effective end-of-service life. It should be noted that the end-of-service indicator acts on absorption and the resulting guidance losses of light in the fiber. As the absorption of gases into the porous outer layer of the fiber depends on the physical and chemical properties of the adsorbate, the extent of absorption, and consequently the sensitivity of the device is different for different toxic gases. Therefore, neither colormetric indicator strips nor optical fiber based indicators are completely non-selective as to the type of toxic environment to which a respirator cartridge is exposed, and consequently have limited applicability.

SUMMARY OF THE INVENTION

The present invention provides an end-of-service indicator for an adsorbent filter wherein saturation of the adsorbent is detected with improved non-selective sensitivity.

This invention also provides an end-of-services indicator for a respirator cartridge or canister containing a gas/vapor sorbent bed wherein the saturation of the sorbent has improved non-selective sensitivity.

Accordingly, the present invention relates to an end-of-service indicator for a sorbent filter comprising:

(a) a tubular housing for insertion into the filter, said housing having first and second ends;

(b) at least one sensor in the housing including an optically transparent support and a coating of noble metal nanoparticles on said support;

(c) a light source at said first end of said housing for irradiating the support;

(d) an opening in said housing intermediate said first and second ends;

(e) a cover on said opening permeable to vapor and impermeable to a solid for admitting vapor into contact with said sensor; and (f) a light detector in said second end of said housing for measuring the amount of light absorbed by the nanoparticles, changes in the amount of light reaching the detector being indicative of the sorptive capacity of the filter.

The indicator of the present invention relies on the fact that noble metal nanoparticles show a characteristic increase in absorbance of light and a red-shift (shift to lower energy level) in the surface plasmon band upon exposure to any chemical vapors with a refractive index different from that of air. These properties are particularly well suited for a generic non-selective chemical vapor sensor. When noble metal nanoparticles are deposited as a homogeneous layer on an optical transparent substrate and coupled with a light detector such as a photodiode or charged-coupled device (CCD) array, the resulting device may be used to detect in real-time any exposure of the film to a chemical vapor. Any change in response of the light detector can be used to warn a user of a decrease in the adsorption efficiency of a respirator cartridge or canister containing an activated carbon or other, non-carbon sorbent, and ultimately that the adsorption efficiency has been exceeded and that toxic chemical vapors may penetrate through the respirator adsorbent cartridge.

DETAILED DESCRIPTION OF THE INVENTION

Figure 1:
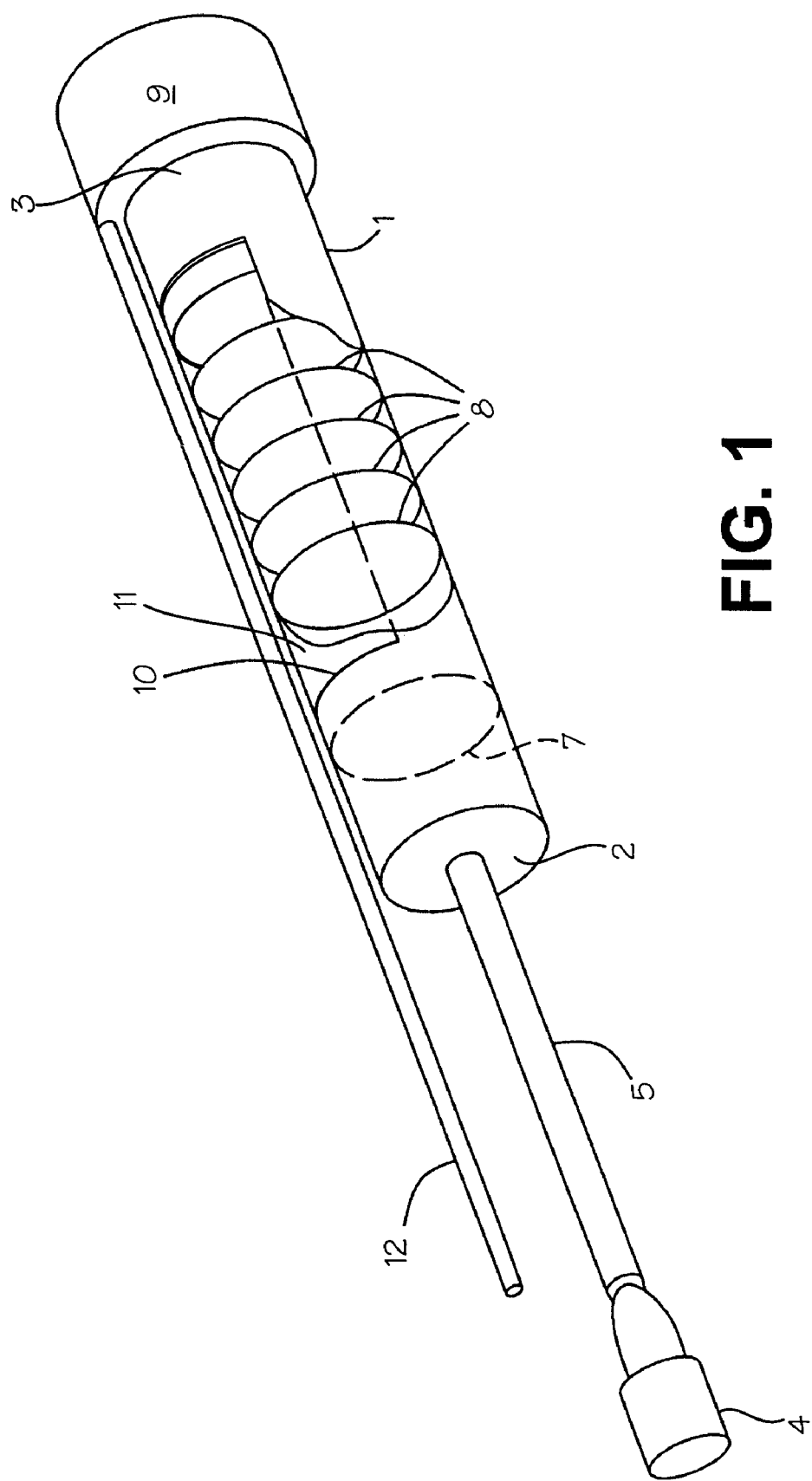
FIG. 1 is a partly sectioned, schematic isometric view of an end-of-service indicator in accordance with the invention.

With reference to FIG. 1, an end-of service indicator for an adsorbent filter includes an elongated, tubular housing 1 of circular cross section with first and second closed ends 2 and 3, respectively. Light from a light source 4, in this case a light emitting diode, enters the end 2 of the housing 1 via a fiber optic cable 5. The light passes through an optional optical filter 7 for tailoring the spectral characteristics of the light and improving the sensitivity of the detector, and then through a plurality of sensors 8 to a light detector 9. The sensors 8 are thin, disc-shaped, optically transparent films or substrates with a homogenous layer of nanoparticles of a noble metal, which is preferably gold or silver. The material used in the film or substrate of sensor 8 can be any transparent, inert material such as glass, quartz glass, sapphire, salt or a polymer. In the present case, the inventors used small pieces of glass microscope slides.

Vapor enters the housing 1 via an opening 10 in the area of the sensors 8. The opening 10 is covered with a polyethylene film 11 which is highly permeable to chemical vapors but impermeable to solid particles. It will be appreciated that any inert, vapor permeable membrane can be used for the film 11. The film 11 prevents blockage of the housing by particles and excess light attenuation. The detector 9, which closes the second end 3 of the housing 1, is defined by a photodiode or charge-coupled device (CCD) array. Signals from the detector 9 are transmitted via output wire 12 to an accompanying electronic processor (not shown).

Figure 2:
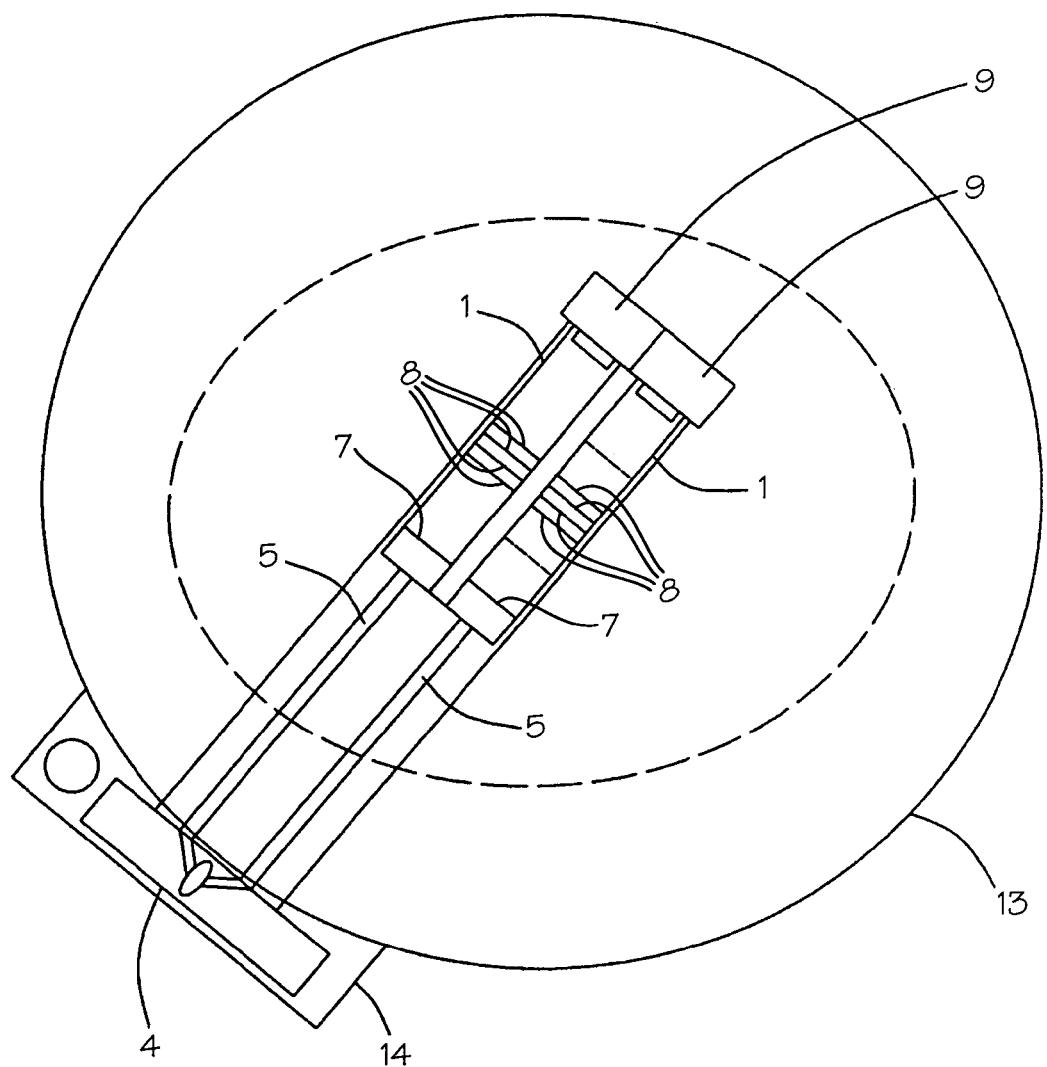
FIG. 2 is a schematic cross-sectional view of a respirator canister containing an indicator according to the invention.

The indicator is inserted into the sorbent bed of a respirator canister 13, whereby chemical vapors accumulate in the bed. Referring to FIG. 2, two indicators can be inserted into the sorbent bed of the canister 13 with the housings 1 extending through the wall of the canister. The housings 1 are embedded in the activated carbon sorbent near the bottom of the bed. The positioning of the indicators within the canister 13 can be varied in order to determine the degree of saturation of the activated carbon at various depths in the bed. Light from the source 4 located in electronics and battery casing 14 is passed to each of the indicators. During experiments using the apparatus of FIG. 2, 2-chloroethyl ethyl sulfide (2-CEES) was injected into the inlet of the canister 13. In the experiments, a one inch diameter tube was attached to the inlet of a C7 canister 13 and air was introduced at a rate of 10 L per minute which is close to a normal breathing rate. The inlet tube of a gas chromatograph system was positioned at the exit of the canister 13. In this configuration, the chromatograph system was used to detect low nanogram amounts of 2-CEES at the exit of the canister 13 to gauge the sensitivity of the detectors.

As illustrated in FIG. 2, each indicator has its own detector 9 and a single light source 4 coupled to the housings 1 by optical fibers 5. One indicator is used as a reference which helps compensate for fluctuations in experimental parameters such as light intensity, and this increases the sensitivity of the overall device. After a warm-up/conditioning period of 55 minutes, 2 ml of 2-CEES was injected into the input of the canister 13 (arrow $A_1$ in FIG. 3A). A second injection of 2-CESS was made 78 minutes later (arrow $A_2$ in FIG. 3A). A standard UV-vis absorption measuring spectrometer equipped with fiber optic light and detector extensions was employed to measure the absorbance of the nanoparticle films.

Figure 3A:
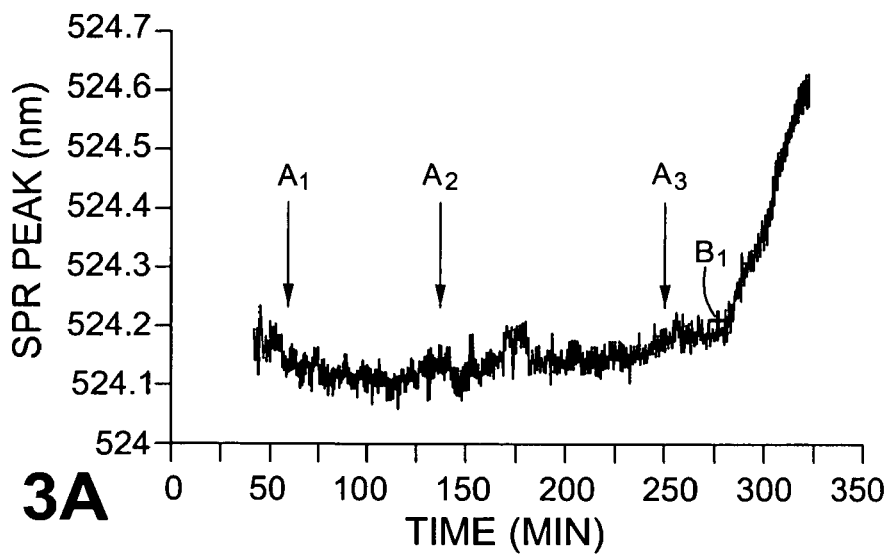
FIG. 3A is a graph illustrating the surface plasmon resonance peak position of a nanoparticle film on a transparent substrate (vertical axis) when exposed to 2-chloroethyl ethyl sulfide vapor over a period of time.

The position of the peak (in nm) of the surface plasmon resonance (SPR) band is plotted along the vertical axis of FIG. 3A. Approximately two hours later after the second injection, a third injection of 2 ml of 2-CEES was made at the inlet of canister 13 (arrow $A_3$ in FIG. 3A). Shortly thereafter (at B1 in the graph of FIG. 3A), the SPR peak position climbed steeply, a clear indication that the nanoparticle films of the sensors 8 were responding to the 2-CEES vapors that had been accumulating within the carbon adsorbent bed of the canister 13. The absorption responses of the nanoparticle films measured at 560 nm are shown in FIG. 3B after 260 minutes as indicated by B2.

Figure 3B:
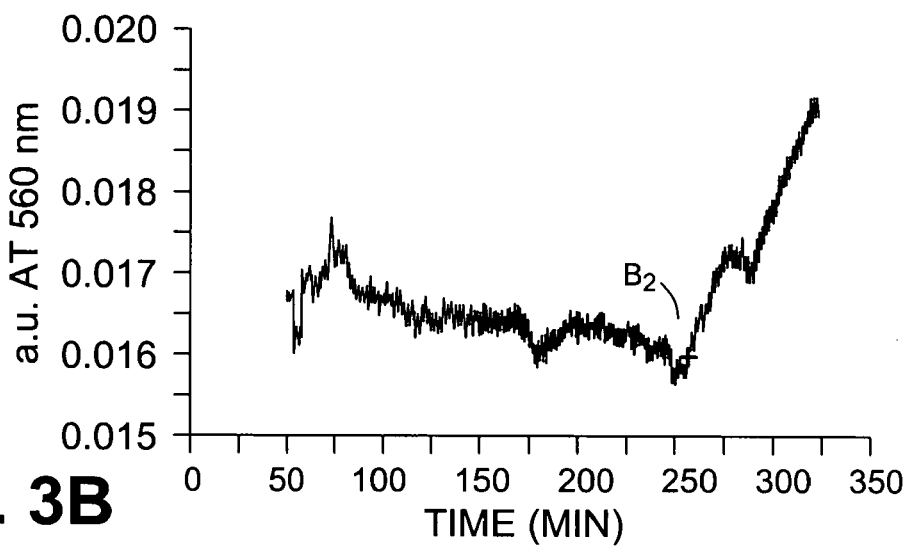
FIG. 3B is a graph illustrating the absorption response of nanoparticle films (vertical axis) when exposed to 2-chloroethyl ethyl sulfide vapor over a period of time.

The time at which increases in the response of nanoparticles occurred are indicated at B1 in FIG. 3A and B2 in FIG. 3B. It should be noted that at the time the responses increased in FIGS. 3A and 3B, the chromatograph system at the outlet of canister 13 showed no signs of detecting the 2-CEES that had been injected into the inlet of canister 13.

Figure 3C:
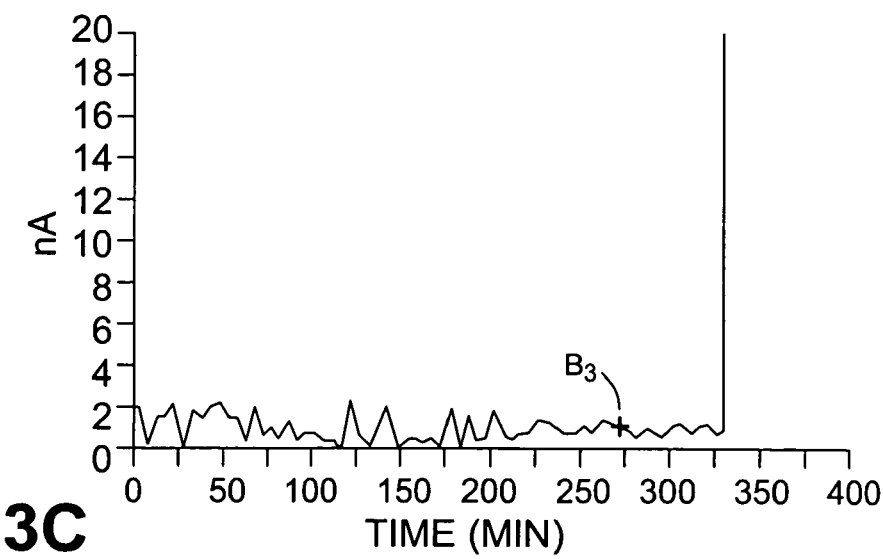
FIG. 3C is a graph illustrating the response of a gas chromatograph to exposure to 2-chloroethyl ethyl sulfide vapor.

To ensure that the chromatograph system was operating properly, at 320 minutes the chromatograph sampling tube was deliberately set near a container of liquid 2-CEES and this is illustrated by the graph in FIG. 3C. FIG. 3C illustrates that the chromatograph system was working and the chromatograph signal climbed to extremely high values after 330 minutes when the sampling tube was set near the container of 2-CEES.

Although the use of the refractive index sensitive nanoparticle films to measure increases in chemical vapor pressure within filter elements have been described in the preferred embodiments for respirator canisters as indicators of depleting adsorption capacity of the adsorbent and vapor penetration, they can be used in other areas where non-selective organic chemical vapor sensors are required to measure increases in chemical vapor pressure, such as in protective shelters to indicate when filters need to be replaced.

The invention claimed is:

1. An end-of-service indicator for a sorbent filter comprising:
   (a) a tubular housing for insertion into the filter, said housing having first and second ends;
   (b) at least one sensor in the housing including an optically transparent support and a coating of noble metal nanoparticles on said support;
   (c) a light source at said first end of said housing for irradiating the support;
   (d) an opening in said housing intermediate said first and second ends;
   (e) a cover on said opening permeable to vapor and impermeable to a solid for admitting vapor into contact with said sensor; and
   (f) a light detector in said second end of said housing for measuring the amount of light absorbed by the nanoparticles, changes in the amount of light reaching the detector being indicative of the sorptive capacity of the filter.

2. The indicator of claim 1 including a plurality of sensors in said housing aligned with each other and with an optical path between said light source and said detector.

3. The indicator of claim 2, wherein said housing is circular in cross section and said sensors are disc-shaped.

4. The indicator of claim 2 including a fiber optic cable extending through said first end of said housing, with said source of light at an outer end of a cable for introducing light into the housing.

5. The indicator of claim 2 including an optical filter in said housing between said light source and said sensors for tailoring the optical characteristics of light from said light source.

6. The indicator of claim 4, wherein the light source is a light emitting diode.

7. The indicator of claim 1, wherein the noble metal nanoparticles are gold nanoparticles.

8. The indicator of claim 7, wherein the gold nanoparticles form a homogenous film on said support.

9. The indicator of claim 7, wherein the noble metal nanoparticles are silver nanoparticles.

10. The indicator of claim 7, wherein the silver nanoparticles form a homogenous film on said support.

11. The indicator of claim 7, wherein said support is formed of a material selected from the group consisting of glass, quartz glass, sapphire, salt and a polymer.

12. The indicator of claim 11, wherein said cover on said opening in the housing is a polyethylene film.

13. The indicator of claim 9, wherein said support is formed of a material selected from the group consisting of glass, quartz glass, sapphire, salt and a polymer.

14. The indicator of claim 13, wherein said cover on said opening in the housing is polyethylene film.

* * * * *